United States Patent [19]

Tsien et al.

[11] Patent Number: 5,439,797
[45] Date of Patent: Aug. 8, 1995

[54] DETECTION OF ANALYTES USING FLUORESCENT ENERGY TRANSFER

[75] Inventors: Roger Y. Tsien, La Jolla; Susan S. Taylor, Del Mar; Stephen R. Adams, Poway; Ying Ji, San Diego, all of Calif.

[73] Assignee: The Regents of the University of California, Oakland, Calif.

[21] Appl. No.: 114,103

[22] Filed: Aug. 30, 1993

Related U.S. Application Data

[63] Continuation of Ser. No. 547,990, Jul. 2, 1990, abandoned.

[51] Int. Cl.[6] ........................................ G01N 33/533
[52] U.S. Cl. .................................... 435/7.21; 435/7.1; 435/15; 436/501; 436/800
[58] Field of Search .................... 435/7.1, 7.21, 15; 436/501, 800

[56] References Cited

U.S. PATENT DOCUMENTS

| | | | |
|---|---|---|---|
| 4,822,733 | 4/1989 | Morrison | 435/6 |
| 4,828,981 | 5/1989 | Maggio | 435/7 |
| 4,868,103 | 9/1989 | Stavrianopoulos | 435/5 |

OTHER PUBLICATIONS

Slice and Taylor, "Expression of the Catalytic Subunit of cAMP-dependent Protein Kinase in *Escherichia coli*," J. Biol. Chem. vol. 264:20940–20946 (1989).
Herman B., "Resonance Energy Transfer Microscopy," Methods in Cell Biology, vol. 30:219–243 (1989).
Jovin et al., "Luminescence Digital Imaging Microscopy," Annu. Rev. Biophys. Biophys. Chem. vol. 18:271–308 (1989).
Brooker G., "Improvements in the Automated Radioimmunoassay for cAMP or cGMP," Methods in Enzymology vol. 159:45–51 (1988).
Fletcher et al., "Direct Cytochemical Localization of Regulatory Subunit of cAMP-Dependent Protein Kinase Using Fluoresceinated Catalytic Subunit," Methods in Enzymology vol. 159:255–267 (1988).
Saraswat et al., "Expression of the Type I Regulatory Subunit of cAMP-dependent Protein Kinase in *Escherichia coli*," J. Biol. Chem. vol. 261:11091–11096 (1986).
Uster and Pagano, "Resonance Energy Transfer Microscopy: Observations of Membrane-bound Fluorescent Probes in Model Membranes and in Living Cells," J. Cell Biol. vol. 103:1221–1234 (1986).
Wu et al., "Conformational Transitions of Cyclic Adenosine Monophosphate Receptor Protein of *Escherichia coli*. A fluorescent Probe Study," Biochemistry vol. 13:2567–2572 (1974).
Fletcher et al., J Biol. Chem 261, 5504–5513 (1986).
McEvily et al., J. Biol. Chem 261, 2593–2598 (1986).
Woodford et al., J. Biol. Chem. 264, 13321–13328 (1989).
Büchler et al., Eur. J. Biochem 188; 253–259 (1990).
First et al., Biochemistry 28, 3598–3605 (1989a).
First et al., Biochemistry 28; 3606–3613 (1989b).

Primary Examiner—David Saunders
Attorney, Agent, or Firm—Robbins, Berliner & Carson

[57] ABSTRACT

The invention provides labeled proteins suitable for determining the presence of cAMP, other second messengers and organic molecules. The proteins are separately labeled with fluorochromes which, when in close spatial proximity, preferably, less than about 6 nm, interact through the transfer of energy from one fluorochrome to the other.

A composition of matter, $(S_1.A)_{n1}(S_2.D)_{n2}$ is provided wherein $S_1$ and $S_2$ are two proteins which are associated in one state and substantially disassociated in another, the equilibrium between which is controlled by the free concentration of an analyte, and A and D are fluorochromes, the emission wavelength of fluorochrome D overlapping the excitation wavelength of fluorochrome A and the distance between A and D being in sufficiently close proximity to allow the radiationless transfer of energy between the fluorochromes. A and D can be selected from a variety of acceptor, donor pairs such as fluorescein and tetramethylrhodamine and derivatives thereof. The concentration of analytes such as cAMP in a sample can be determined by contacting the sample with $(S_1.A)_{n1}(S_2.D)_{n2}$ providing energy near the excitation wavelength of D and measuring the fluorescence of A or D, the concentration of cAMP and other said analytes being determined by the ratio of emission of D to the emission of A, previously calibrated with reference solutions of known analyte concentration.

60 Claims, 4 Drawing Sheets

FIG. 1

Fluorescence Detection of Cyclic AMP

DETECTION OF ANALYTES USING FLUORESCENT ENERGY TRANSFER

This invention was made with Government support under Grant Nos. GM31004 and GM19301 awarded by the National Institute of General Medical Science and Grant No. NS27177 awarded by the National Institute of Neurological and Communicable Diseases. The Government has certain rights in this invention.

This application is a continuation of Ser. No. 07/547,990, filed Jul. 2, 1990, abandoned.

BACKGROUND OF THE INVENTION

This invention relates to energy transfer between fluorochrome labeled proteins to determine analyte concentration and, more particularly, to methods of determining cAMP concentration using labeled cAMP dependent protein kinase.

The function of many biological molecules is mediated through interactions with proteins and protein complexes. Many of these molecules are found in extremely small concentrations within a living cell. However, their concentration may transiently change in response to physiological stimuli. In many instances, it is important to determine the concentration of such molecules to assess the metabolic state of a cell, hormonal responses and certain diseases. Even if the level changes several fold, at such minute concentrations, such change is not detectable.

One such important molecule which mediates biological function through protein interaction is cyclic AMP (cAMP, adenosine 3', 5'-cyclic monophosphate). Cyclic AMP regulates intracellular reactions in all procaryotic and nucleated animal cells that have been studied to date. It functions as a ubiquitous intracellular mediator, or second messenger, of a variety of hormone induced effects, the first messenger being the extracellular hormone. Such hormone induced effects mediated by increased cAMP levels include, for example, triglyceride breakdown in a fat tissue induced by epinephrine, adrenocorticotropic hormone (ACTH), glucagon or thyroid-stimulating hormone (TSH); water resorption in the kidney by vasopressin; glycogen breakdown in the muscle and liver; increased heart rate by epinephrine and progesterone secretion by the ovary in response to luteinizing hormone. These differential responses to cAMP are induced by hormone-receptor interactions at the cell surface and result in the intracellular synthesis of cAMP. Thus, different target cells respond to increases in cAMP levels in different but characteristic way.

For cAMP to function as a second messenger, its intracellular concentration must be tightly controlled and able to change rapidly in response to hormone-receptor binding. Normally, cAMP levels are less than about 1 $\mu$M and increase approximately five-fold upon hormonal stimulation. The increase in cAMP levels is due to synthesis by the enzyme adenylate cyclase from ATP. Following this transient increase, cAMP levels are rapidly returned to normal levels through the action of phosphodiesterases.

To effectively study cAMP dependent hormonal responses and their physiological mechanisms, it is necessary to accurately measure small concentrations of cAMP. More essentially, it is important to measure free cAMP concentrations, since in general, the biological activity of intracellular messengers is controlled by and correlates with the concentrations of free messenger, whereas total concentrations measured after tissue disruption include material bound to biologically irrelevant sites. Previous methods for measuring cAMP concentrations employed classical competitive binding assays such as radioimmunoassays, and required the manipulation and preparation of extracts from thousands or millions of cells. These methods resulted in poor spatial and temporal resolution and were incapable of distinguishing free or biologically active cAMP levels from total or sequestered cAMP. Moreover, these methods required the use of hazardous, perishable isotopes and were therefore expensive.

Additionally, second messengers other than cAMP such as cyclic GMP (cGMP), calcium and diacylglycerol as well as other organic molecules such as tumor-promoting phorbol esters are of great importance in signal transduction and cell physiology. Accurate determination of the biologically active concentrations of these molecules is also necessary to effectively study hormonal responses and physiological mechanisms. However, except for simple inorganic ions such as calcium, there is no indicator system such as to measure the biologically active concentrations of these molecules. Most of the same drawbacks that exist for determining free cAMP concentrations within the cell exist for these molecules as well.

Thus, there exists a need for a method to rapidly, efficiently and non-destructively measure free intracellular cAMP concentrations as well as other organic molecules in single living cells. Such an invention would be of critical importance to the understanding of hormonal regulation. The present invention satisfies this need and provides related advantages as well.

SUMMARY OF THE INVENTION

The invention provides labeled proteins suitable for determining the presence of cAMP, other second messengers and organic molecules. The proteins are separately labeled with fluorochromes which, when in close spatial proximity, preferably, less than about 6 nm, interact through the transfer of energy from one fluorochrome to the other.

A composition of matter, $(S_1\text{-}A)_{n1}(S_2\text{-}D)_{n2}$ is provided wherein $S_1$ and $S_2$ are two proteins which are associated in one state and substantially disassociated in another, the equilibrium between which is controlled by the free concentration of an analyte, and A and D are fluorochromes, the emission wavelength of fluorochrome D overlapping the excitation wavelength of fluorochrome A and the distance between A and D being in sufficiently close proximity to allow the radiationless transfer of energy between the fluorochromes. A and D can be selected from a variety of acceptor, donor pairs such as fluorescein and tetramethylrhodamine and derivatives thereof. The concentration of analytes such as cAMP in a sample can be determined by contacting the sample with $(S_1\text{-}A)_{n1}(S_2\text{-}D)_{n2}$ providing energy near the excitation wavelength of D and measuring the fluorescence of A or D, the concentration of cAMP and other said analytes being determined by the ratio of emission of D to the emission of A, previously calibrated with reference solutions of known analyte concentration.

DETAILED DESCRIPTION OF THE INVENTION

As used herein, the term "protein" or "subunit" indicates a linear sequence of amino acids which exhibits biological function. This linear sequence includes native proteins, domains of proteins and fragments of proteins so long as function is maintained. The term also includes polypeptides and peptides.

As used herein, the term "associated" refers to two proteins such as subunits of an enzyme, which are in contact with each other. The contact region may include all or parts of the two molecules. Therefore, the term "substantially disassociated" or "disassociated" refers to the loss of contact between the associated regions, including loss of all contact regions such that the proteins are completely separated as well as the loss of some regions so that the body of the proteins are no longer in close proximity to each other but may still be tethered together. The term "complex" as used herein, refers to the proteins or subunits when they are in the associated state. The complex may include more than one molecule of each of the two proteins.

As used herein, the term "cAMPdPK" refers to the cyclic AMP dependent protein complex as described in Alberts et al., (1989), Molecular Biology of the Cell, Garland Publishing, Inc., and in Slice and Taylor, (1989), J. Biol. Chem. 264:20940–20946, both of which are herein incorporated by reference. The complex consists of two proteins which perform regulatory and catalytic functions. It is intended that the term will include all isotypes of the regulatory and catalytic proteins.

As used herein, the term "fluorochrome" refers to a molecule which is capable of absorbing energy at a certain wavelength range and releasing the energy at a wavelength range other than the absorbance range. Therefore, the term "excitation wavelength" refers to the range of wavelengths that a fluorochrome absorbs energy. The term "emission wavelength" includes to the range of wavelengths that a fluorochrome releases energy or fluoresces. The term fluorochrome also includes derivatives thereof, such as chemical moieties for attachment to proteins. Examples of fluorochromes are fluorescein and tetramethylrhodamine. A derivative of each is fluorescein isothiocyanate and tetramethylrhodamine isothiocyanate.

As used herein, the term "sample" refers to a material, such as a solution, extract or intact cell suspected of containing an analyte.

As used herein, the term "labeling" refers to the attachment of a chemical moiety such as a fluorochrome to a protein. The attachment is typically through a covalent bond but may also include non-covalent interactions as well. Therefore, the term "labeled proteins" refers to proteins which have chemical moieties such as fluorochromes attached to them.

The invention provides a composition of matter, comprising $(S_1.A)_{n1}(S_2.D)_{n2}$ wherein $S_1$ and $S_2$ are two proteins which are associated in one state and substantially disassociated in another state, and D and A are different fluorochromes, the emission wavelength of one fluorochrome overlapping the excitation wavelength of the other fluorochrome, the distance between D and A is in sufficiently close proximity to allow the radiationless transfer of energy between the fluorochromes, and n1 and n2 representing the stoichiometry of said proteins, and wherein $S_1$ or $S_2$ is capable of binding an analyte X, the binding of X affects the affinity of $S_1$ and $S_2$ for each other.

The two proteins $S_1$ and $S_2$ which are labeled with fluorochromes are typically subunits of an enzyme but may include any two proteins which exhibit associated and substantially disassociated states. Examples of such protein pairs include the subunits for cAMP dependent protein kinase (cAMPdPK), the subunits of GTP-binding proteins, calmodulin and calmodulin dependent protein kinases and the regulatory and catalytic domains of protein kinase C.

When in the associated state, the subunits form a protein complex such as a holoenzyme. The number of proteins within the complex can vary depending on the stoichiometry between $S_1$ and $S_2$. Additionally, the complex may include proteins other than $S_1$ and $S_2$. These other proteins within the complex may be considered as components of $S_1$ or $S_2$ so long as they maintain a stable association with either $S_1$ or $S_2$.

When in the disassociated state, at least one of the proteins will have substantially changed its distance from the other protein. For example, the disassociated state for cAMPdPK consists of free catalytic and regulatory proteins or subunits. Likewise, GTP-binding proteins are disassociated into alpha and beta-gamma subunits, calmodulin dependent protein kinases disassociate from calmodulin, and protein kinase C regulatory and catalytic domains initially move apart and are subsequently separated by proteolysis.

Radiationless energy transfer is based on the biophysical properties of fluorochromes. These principles are reviewed in Lakowicz, J., 1983. Principles of Fluorescence Spectroscopy, Plenum Press, New York and Jovin and Jovin, 1989, in Cell Structure and Function by Microspectrofluorometry, edited by E. Kohen and J. G. Hirschberg, Academic Press, both of which are incorporated herein by reference. Briefly, a fluorochrome absorbs light energy at a characteristic wavelength. This wavelength is also known as the excitation wavelength. The energy absorbed by a fluorochrome is subsequently released through various pathways, one being emission of photons to produce fluorescence. The wavelength of light being emitted is known as the emission wavelength and is an inherent characteristic of a particular fluorochrome. Radiationless energy transfer is the quantum-mechanical process by which the energy of the excited state of one fluorochrome is transferred without actual photon emission to a second fluorochrome. That energy may then be subsequently released at the emission wavelength of the second fluorochrome. The first fluorochrome is generally termed the donor (D) and has an excited state of higher energy than that of the second fluorochrome, termed the acceptor (A). The essential features of the process are that the emission spectrum of the donor overlap with the excitation spectrum of the acceptor, and that the donor and acceptor be sufficiently close. The distance over which radiationless energy transfer is effective depends on many factors including the fluorescence quantum efficiency of the donor, the extinction coefficient of the acceptor, the degree of overlap of their respective spectra, the refractive index of the medium, and the relative orientation of the transition moments of the two fluorochromes, but is typically 4–6 nm for favorable pairs of donor and acceptor. Beyond the optimum range of intermolecular distances, the energy transfer efficiency falls off as the inverse sixth power of the distance.

The analyte X capable of being bound by either $S_1$ or $S_2$, can be, for example, a second messenger such as cAMP, calcium, cGMP, and diacylglycerol; relevant hormone-receptor complexes; or an organic molecule such as phorbol ester. When bound to such molecules, $S_1$ and $S_2$ may be in either the associated or disassociated states.

The invention provides a composition of matter wherein $S_1$ and $S_2$ are proteins, or subunits of a complex, such as a holoenzyme. Such holoenzymes can be, for example, cAMPdPK, GTP-binding proteins, calmodulin dependent protein kinase and protein kinase C.

In one embodiment, the invention also provides a composition of matter wherein $S_1$ is the regulatory subunit of cAMPdPK and $S_2$ is the catalytic subunit of cAMPdPK and are labeled with different fluorochromes such that the emission wavelength of one overlaps the excitation wavelength of the other.

Figure 1:
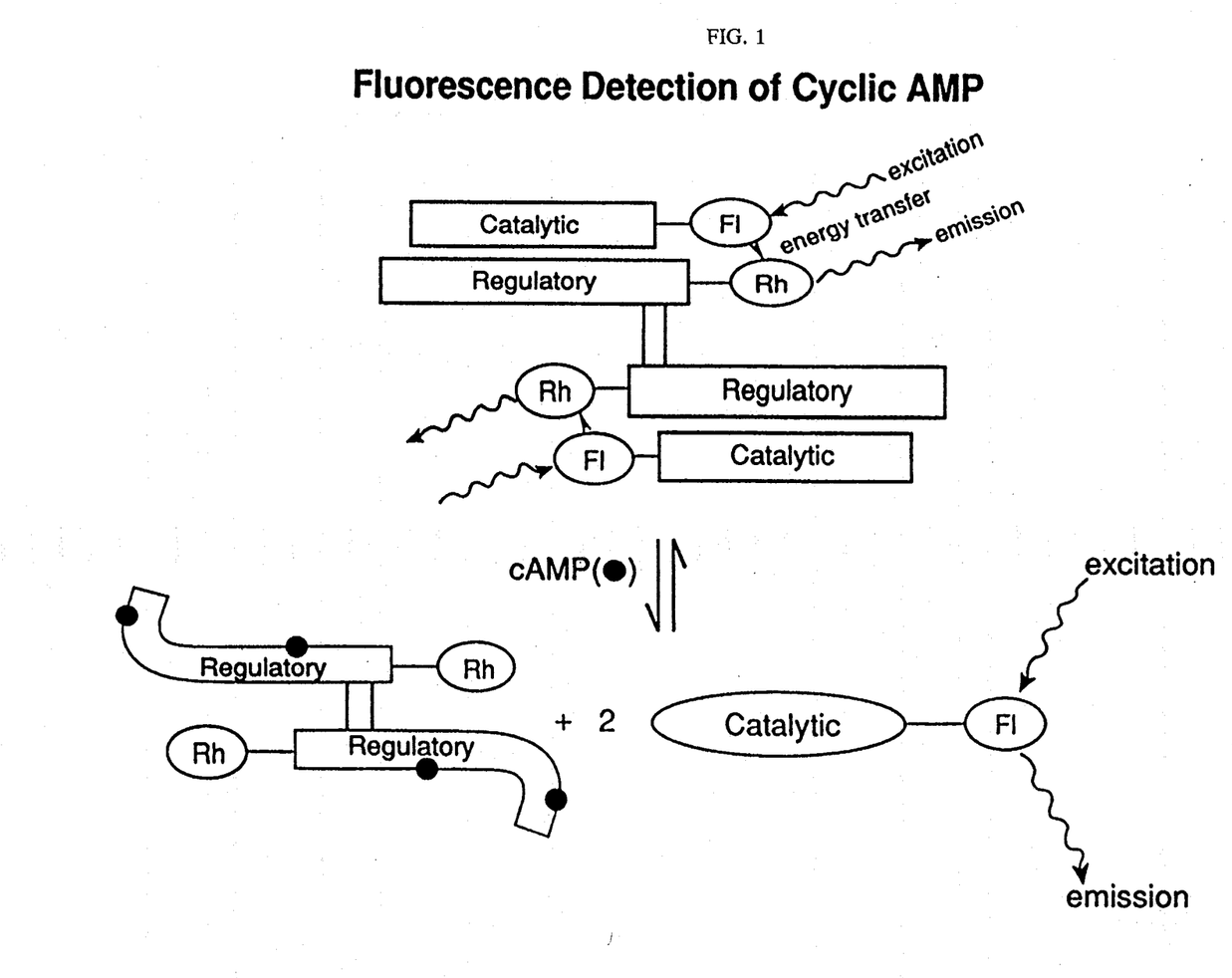
FIG. 1 is a schematic diagram depicting the use of fluorescence energy transfer to measure cAMP.

For example, in the absence of cAMP, the regulatory (R) and catalytic (C) subunits of cAMPdPK have a stoichiometry of $R_2C_2$ as shown in FIG. 1. The complex is inactive as a kinase, since the R subunits inhibit the kinase domains of the C subunits. Upon the binding of cAMP by R, the R subunits dissociate from the C subunits, releasing the biological activity of the latter. The invention includes labeling the R subunits with one fluorochrome and the C subunits with a different fluorochrome, such that in the intact $R_2C_2$ complex, light energy absorbed by one fluorochrome is transferred to the other fluorochrome by the process of radiationless energy transfer. This phenomenon requires that the wavelengths of fluorescent emission from one fluorochrome, the donor (D), overlap the wavelengths of excitation of the other fluorochrome, the acceptor (A), and that the D and A moieties be in sufficiently close proximity to allow the radiationless transfer of energy between the fluorochrome pairs. In the case of fluorescein and tetramethylrhodamine, this distance is less than about 4 to 6 nm. For other fluorochrome pairs, the distance can be determined by those skilled in the art. Provided suitable choices are made for D and A, this condition of close proximity is reasonably well satisfied in a holoenzyme complex such as that for cAMPdPK, so that energy transfer occurs with considerable efficiency.

The transferred energy is easily detectable by excitation at wavelengths absorbed by D, since emission from D is quenched and the energy appears instead at longer wavelengths characteristic of A's emission.

Subunits R.D and C.A can be paired to make $(R.D)_2(C.A)_2$, or R.A and C.D can be combined into $(R.A)_2(C.D)_2$, where . denotes attachment of the indicated fluorochrome. Once cAMP has dissociated R from C, D and A thereby become widely separated from each other and unable to transfer energy from D to A. With the subunits dissociated, illumination at wavelengths absorbed by D simply causes fluorescence emission from D, with no involvement of A, so that the composite emission spectrum shifts towards the shorter wavelengths of D.

Holoenzyme labeled with two different fluorochromes as described above is found to have essentially identical sensitivity to cAMP as the native holoenzyme. This property allows the use of protein complexes such as cAMPdPK to be used as measuring devices or sensors for a variety of biological molecules. Moreover, it guarantees that the sensor has the optimal affinity for such biological molecules as cAMP, for example, since native holoenzyme is the main endogenous sensor for cAMP and the concentrations of interest are precisely those which affect this enzyme. Moreover, the activity of labeled enzyme as a kinase upon stimulation by cAMP is found to be identical to native holoenzyme likewise stimulated. This property is valuable because it minimizes any perturbation of the biological effectiveness of cAMP within cells into which the sensor has been introduced. If the sensor were not an effective kinase, then any cAMP bound to it would be prevented from exerting biological activity so that the sensor would inherently inhibit the signaling pathway whose activity was to be measured. However, if the sensor is a normal kinase, cAMP molecules bound to it are biologically fully effective and not removed from mediating such events.

The invention also provides a method of determining the concentration of an analyte in a sample comprising the steps of: (a) labeling proteins $S_1$ and $S_2$ with fluorochromes A and D, where $S_1$ or $S_2$ is capable of binding the analyte and $S_1$ and $S_2$ are associated in one state and substantially disassociated in another state, the equilibrium of which is controlled by the concentration of free analyte, the fluorochromes are selected such that the emission wavelength of one fluorochrome overlaps the excitation wavelength of the other fluorochrome to form labeled proteins $(S_1D)_{n1} (S_2A)_{n2}$ or $(S_1A)_{n1} (S_2D)_{n2}$; (b) contacting the labeled proteins with the sample; (c) providing energy near the excitation wavelength of D or A; (d) measuring the fluorescences emitted at the emission wavelengths of A and D respectively, and determining the extent of energy transfer from D to A by the ratio of their emission amplitudes, or by the fluorescence lifetime of D, or by the rate of photobleaching of D. Any of these parameters, but most conveniently the ratio of emission amplitudes, can be related to the analyte concentration by a calibration curve established with samples of known analyte concentration.

In one embodiment, holoenzyme labeled with fluorescein on the C subunit and tetramethylrhodamine on the R subunit, for example, can be used to measure the concentration of cAMP in vitro and in vivo. For the former, the enzyme is titrated with cAMP while measuring its fluorescent emission following excitation at 490 to 500 nm. A plot of the emission ratio (520:580 nm are the optimal wavelengths) against known concentrations of cAMP can be used as a standard curve for determining cAMP concentrations in unknown solutions under the same conditions. To measure in vivo cAMP concentrations inside living cells requires incorporation of the labeled holoenzyme into the cells of interest by microinjection, electroporation, lipofection, bead loading, scrape loading or any other comparable and well-known technique. Such methods are described in Riabowol et al., (1988) Cold Spring Harbor Symposia on Quantitative Biology 53:85–90; Sambrook et al., Molecular Cloning: A Laboratory Manual, (1989) Cold Spring Harbor Laboratory and Ausubel et al., Current Protocols in Molecular Biology, (1987), John Wiley and Sons, all of which are incorporated herein by reference. Excitation at 490 to 500 nm on a fluorescence microscope and detection of the emission near the two optimal wavelengths (520 and 580 nm) is achieved by a photometer or television camera. Calibration of the minimum and maximum ratio values is achieved by first setting the zero cAMP concentration value by addition of a cAMP antagonist, adenosine -3', 5'-cyclic monophosphothioate, Rp-isomer (Rp-cAMPS) which inhibits dissociation of the holoenzyme. Subsequent removal of the cAMP antagonist and addition of the membrane-permeable cAMP analog gives complete dissociation and hence intermediate cAMP values can be determined using the standard curve derived in vitro.

Currently preferred choices of fluorochromes are fluorescein for the donor dye, which has emission wavelengths of about 510 to 550 nm, and tetramethylrhodamine for the acceptor, which has excitation wavelengths of about 510 to 550 nm, both being attached to the subunits via isothiocyanates under conditions to favor reaction with lysines. However, a variety of fluorochromes and derivatives thereof can be used so long as the emission wavelength of fluorochrome D overlaps the excitation wavelength of fluorochrome A and results in energy transfer from D to A. For example, D and A fluorochrome pairs may be a 7-aminocoumarin and dipyrromethene-borate, an indocarbocyanine and rhodamine X, or a phycoerythrin and allophycocyanin.

The invention also provides for a method of preparing a complex comprising protein subunits $S_1$ and $S_2$ which are associated in one state and substantially disassociated in another state, the equilibrium between which is controlled by the concentration of a free analyte X, and wherein $S_1$ or $S_2$ is capable of binding the analyte, comprising: (a) attaching fluorochrome A to $S_1$, said fluorochrome A having an excitation wavelength which overlaps with the emission wavelength of a second fluorochrome D; (b) attaching the second fluorochrome D to $S_2$; (c) mixing the labeled subunits so that a complex is formed wherein the fluorochromes are in sufficiently close proximity to allow radiationless transfer of energy between the fluorochromes; and (d) recovering the labeled subunits as a complex.

In one embodiment, R and C are separately available as recombinant proteins, for example from expression in *E. coli*, which are then labeled. However, careful adjustment of reaction conditions is necessary so that the act of labeling does not prevent reassociation into holoenzyme or subsequent cAMP sensitivity and kinase activity. Previous literature has suggested that labeling isolated C with fluorescein isothiocyanate ruined its ability to combine with R; under milder conditions, however, C was not damaged as described below.

The invention additionally provides a method of preparing a complex comprising protein subunits $S_1$ and $S_2$ which are associated in one state and substantially disassociated in another state, the equilibrium between which is controlled by the concentration of a free analyte X, and wherein $S_1$ or $S_2$ is capable of binding the analyte, comprising: (a) attaching fluorochrome A to a complex comprising $S_1$ and $S_2$, said fluorochrome A having an excitation wavelength which overlaps with the emission wavelength of a second fluorochrome D; (b) attaching the second fluorochrome D to a second complex comprising $S_1$ and $S_2$; (c) separating the subunits of said first and second complex to obtain labeled subunits $S_1.D$, $S_2.D$, $S_1.A$ and $S_2.A$; and (d) mixing the labeled subunits wherein said fluorochromes are in sufficiently close proximity to allow radiationless transfer of energy between the fluorochromes to form label complexes $(S_1.D)_{n1}(S_2.A)_{n2}$ or $(S_2.A)_{n1}(S_2.D)_{n2}$, wherein n1 and n2 represent the stoichiometry of the labeled subunits.

An alternative method is to label pre-formed holoenzyme $R_2C_2$ with D, thereby preparing $(R.D)_2(C.D)_2$ in which the sites of interaction between R and C are inherently protected. A separate batch of $R_2C_2$ is analogously labeled with A to make $(R.A)_2(C.A)_2$. Then labeled R and labeled C are dissociated and separated from each other by passage through a cAMP affinity column, to which labeled R sticks while labeled C passes through. R can be recovered from the column by elution with free cAMP. When this separation is applied to each batch, one obtains R.D, C.D, R.A, and C.A, which are then recombined in different pairings to make $(R.D)_2(C.A)_2$ as one preparation and $(R.A)_2(C.D)_2$ as another.

The holoenzyme or individual subunits of cAMPdPK can be prepared from mammalian sources such as that described by Bubis et al., (1985) Biochemistry, 24:2163–2170, and Zick et al., J. Biol. Chem., (1982) 257:2287–2293, both of which are herein incorporated by reference. If subunits from recombinant or mammalian sources are used for the preparation of holoenzyme then reconstitution can be performed as described in the Examples.

The following examples are intended to illustrate but not limit the invention.

EXAMPLE I

Recombinant Expression and Purification of cAMP-Dependent Protein Kinase Regulator Subunit Reagents were purchased from the following companies: histone IIA, phenylmethylsulfonyl fluoride, isopropyl-β-D-thiogalactopyranoside (IPTG), and bovine serum albumin, (Sigma, St. Louis, Mo.); $N^\alpha$-p-tosyl-L-lysine chloromethyl ketone and cAMP, (United States Biochemical Corp., Cleveland, Ohio.); 2,8-[$^3$H]cAMP (27 Ci/mmol) and 8-$N_3$[$^{32}$P]cAMP (20–30 Ci/mmol), (ICN); Sephadex G-150 and cAMP-agarose ($N^6$- ethane spacer), (Pharmacia, Pleasant Hill, Calif.); nitrocellulose (0.45 μm) and electrophoresis reagents, (Bio-Rad, Richmond, Calif.); and Cytoscint, (West Chem). Enzymes used in DNA manipulations were obtained from either Bethesda Research Laboratories (Gaithersberg, Md.) or Boehringer Mannheim (Indianapolis, Ind.) and were used according to the manufacturer's specifications. Fluorescent labels were obtained from Molecular Probes (Eugene, Oreg.) and cAMP analogs were obtained from Biolog (La Jolla, Calif.). All other reagents were analytical grade.

Plasmid 62C12, Lee et al., (1983) Proc. Natl. Acad. Sci. U.S.A., 80:3608–3612, and herein incorporated by reference, which contains the full-length cDNA of bovine $R^1$ in pBR322 was subcloned into pUC7, Viera et al., (1982) Gene, 19:259–268, and herein incorporated by reference for cDNA expression.

For subcloning, DNA manipulations were carried out according to Maniatis et al., (1982) Molecular Cloning: A Laboratory Manual, Cold Spring Harbor Laboratory, Cold Spring Harbor, N.Y., and herein incorporated by reference. Briefly, 62C12 was digested with NarI, and the 3.6-kilobase (kb) fragment containing the cDNA was isolated. Following partial digestion with NcoI, the two large fragments, the full-length cDNA fragment (1155) base pairs (bp), and a truncated fragment (1020 base pairs) were isolated as a mixture, filled-in with Klenow fragment, and ligated into pUC7 that had been linearized with Hinc II. The 135-base pair fragment also was isolated, radiolabeled with [gamma-$^{32}$P]ATP, and used to identify those clones which contained the full-length insert. Twenty colonies were selected, and the DNA from each was prepared and digested with Bg/I in order to establish the orientation of the insert. The DNA from three clones gave a restriction pattern which indicated that the $R^1$ coding segment was inserted in the correct orientation with regard to the lac Z' gene. These clones were further characterized for expression of the protein.

Since basal levels of cAMP are high in E. coli, the following method was devised for the accurate detection of R in crude extracts independent of exogenous cAMP. This method could be used for rapid screening. Protein samples were electrophoresed on 12.5% polyacrylamide gels (1.5 mm) containing sodium dodecyl sulfate according to the method of Laemmli (1970) Nature 227:680–685. Proteins were then transferred from the gels to nitrocellulose filters using an electroblotting apparatus (Hoefer Scientific Instruments). Gels were electrotransferred for 4 to 6 hours at 500 mA in 20 mM Tris, 154 mM glycine, 20% methanol (pH 8.3). The nitrocellulose was incubated for 1 hour at room temperature with 0.05% Tween 20 in 150 mM sodium chloride and 10 mM Tris (pH 7.5) and then washed at room temperature with the same buffer except that Tween 20 was omitted. The filter was incubated with 8-N$_3$[$^{32}$P]cAMP (20 nM) in the same buffer for 30 minutes in the dark at room temperature. After washing with ice-cold buffer, the filter was irradiated with UV S-11 lamp (254 nm) for 5 minutes, washed again, blotted dry, and subjected to autoradiography. The R-subunit also was detected by Millipore filtration using 2,8-[$^3$H]cAMP as described by Kerlavage et al., (1982) J. Biol. Chem., 257:1749–1754, and herein incorporated by reference.

Purification of the regulatory subunit was performed by inoculating 5 mls of L-broth containing ampicillin (50 μg/ml) with the highest expressing transformant and growing at 37° C. until the cell density reached OD$_{550}$=0.1–0.5. The culture was then transferred to 1 liter of L-broth containing ampicillin and incubated (12 to 16 hours). Unless indicated, all subsequent procedures were carried out at 4° C. the cells were centrifuged at 5,000×g for 30 minutes, and the resulting pellet was resuspended in buffer I (20 mM potassium phosphate, 5 mM EDTA, 5 mM 2-mercaptoethanol, 15 mg/liter N$^α$-p-tosyl-L-lysine chloromethyl ketone, and 15 mg/liter phenylmethylsulfonyl fluoride). This suspension was passed through a French pressure cell twice and then centrifuged at 5,000×g for 20 minutes. The pellet was re-extracted with the same buffer. Ammonium sulfate was added slowly to the pooled supernatant fractions until a concentration of 70% was reached. After 1 hour, the precipitated protein was recovered by centrifugation at 12,000×g for 30 minutes, redissolved in buffer I, and dialyzed against the same buffer overnight. Fractions were assayed for [$^3$H]cAMP binding and analyzed by polyacrylamide gel electrophoresis followed by photolabeling as described above. The dialyzed sample was then added to cAMP-agarose and gently rotated overnight. After removing the supernatant solution, the resin was washed with buffer I containing 2M NaCl until the absorbance at 280 nm reached 0 and then washed again with buffer I. The R-subunit was eluted with 2 volumes of cAMP (50 mM) in buffer I at 30° C. for 1 hour. The elution was repeated at least once.

The eluate from the cAMP-agarose resin frequently contained some proteolytic degradation products of R in addition to full-length R, which was separated on a 70 cm Sephadex G-150 column equilibrated and eluted with 25 mM potassium phosphate, 5mM 2-mercaptoethanol, 5mM EDTA, and 150 mM NaCl (pH 6.5). Fractions (2 ml) were collected at a flow rate of 7 ml/hour. The R-subunit eluted close to the void volume and was well-resolved from the 35-kDa proteolytic fragment.

The recombinant cAMP dependent regulatory subunit was sequenced on an Applied Biosystems Gasphase Sequencer. Two nanomoles of R-subunit were sequenced, and the phenylthiohydantoin derivatives were analyzed on a Beckman HPLC system using a cyano column (IBM) according to the procedure of Hunkapillar and Hood, (1983) Methods Enzymol., 91:486–493, and herein incorporated by reference.

EXAMPLE II

Recombinant Expression and Purification of cAMP-Dependent Protein Kinase Catalytic Subunit Plasmid containing the full length clone for the α catalytic subunit of murine cAMP-dependent protein kinase, pMCO, Uhlen et al., (1986) Proc. Natl. Acad. Sci. USA, 83:1300–1304, which is incorporated herein by reference, was subcloned into M13 mp18 for mutagenesis. The bacterial expression vector, pT7-7, Tabor and Richardson, (1985) Proc. Natl. Acad. Sci. USA, 82:1074–1078, and herein incorporated by reference was used for recombinant expression. The E. coli strains used to express the catalytic subunit were: JM101, 222, K38 and BL21 (DE3).

Before introducing a unique NdeI restriction site into the catalytic subunit gene at the initiation methionine, the 1.9-kilobase SacI fragment from pMCO containing the coding region for the catalytic subunit was excised and religated into the SacI site of M13mp18. Single stranded DNA was prepared and used as template for oligonucleotide-directed mutagenesis with a 24-base oligonucleotide (5'-CACGCCGCCCATATGG-GCAACGCC-3') according to the procedure described by Zoller and Smith, (1984) DNA 3:479–488, and herein incorporated by reference. The mutation was verified by dideoxy sequencing according to Sanger et al., (1980) J. Mol. Biol. 143:161–178, and herein incorporated by reference and by mapping with restriction enzymes.

Construction of pLWS-3 was performed by excising a 1988-base fragment from the M13 construct described above with NdeI and HindIII, purified from an agar gel, and ligated into the NdeI-HindIII restriction sites of pT7-7. This ligation mixture was used to transform E. coli JM101 using the procedure described by Maniatis et al., ibid.

Transformants were selected and screened for plasmid DNA containing the cDNA insert following digestion with NdeI and HindIII. DNA was isolated from this plasmid, pLWS-3, and the sequence confirmed by mapping with restriction enzymes and by sequence analysis. The plasmid was then used to transform E. coli BL21(DE3), and transformants were screened for expression of the catalytic subunit by monitoring for the appearance of a 38-40 kDa band following polyacrylamide gel electrophoresis.

For expression of the catalytic subunit, one liter of L-broth (10% Tryptone, 5% yeast extract, and 5% NaCl) containing ampicillin was inoculated with 5 ml of a stationary phase culture of BL21(DE3) transformed with pLWS-3 and grown at 37° C. with vigorous shaking until an absorbance of 0.5 at 590 nm was reached. After adding isopropyl-β-D-thiogalactopyranoside to a final concentration of 0.5 mM, the cells were grown for an additional 3 hours at 37° C. and then harvested by centrifugation.

Purification of the recombinant catalytic subunit was performed by resuspending the pellet in 6 ml of lysis buffer (30 mM MES, pH 6.45, 50 mM KCl, 1 mM EDTA, and 5 mM β-mercaptoethanol) at 4° C. and passed twice through a French pressure cell. Additional lysis buffer was added to bring the total volume to 30 ml. After centrifugation at 12,000×g for 15 minutes at 4° C., the supernatant was removed and diluted with ice-cold water until the conductivity was below 1.3 mmhos. The diluted supernatant was applied to a phosphocellulose column (Whatman P11, 2.0×8.0 cm) pre-equilibrated with buffer I (30 mM MES, pH 6.45, 1 mM EDTA). After washing with the equilibration buffer until the absorbance at 280 nm was 0, the catalytic subunit was eluted with a linear gradient of buffer I (50 ml) to 0.5M potassium phosphate, pH 7.0 (50 ml). Two-ml fractions were collected, and those containing kinase activity were pooled. The protein was precipitated by the batchwise addition of solid $NH_4SO_4$, with constant stirring, until the solution was 80% saturated. The precipitate was collected by centrifugation at 12,000×g for 20 minutes and then resuspended in 0.8 ml of $H_2O$. After removing the undissolved material by centrifugation, the protein solution was loaded onto an Ultrogel AcA 44 (LKB) gel filtration column (1.0×116 cm) equilibrated with 25 mM potassium phosphate, pH 6.8. The fractions containing kinase activity were combined and concentrated to 1 mg/ml by ultrafiltration using an Amicon apparatus and a PM-30 membrane. Based on polyacrylamide gel electrophoresis carried out in the presence of sodium dodecyl sulfate (SDS) according to Laemmli, (1970) Nature 227:680-685, which is incorporated herein by reference, the recombinant catalytic subunit was nearly homogeneous, and the yield was 3.5 to 4.0 mg/liter of culture.

Recombinant catalytic subunit was diluted to 0.04 mg/ml with 20 mM Tris, pH 7.5. Fifty-μl aliquots were kept on ice and then placed in a 49° C. water bath. At the indicated times, tubes were removed, placed on ice, and assayed for stability of the recombinant protein.

Isoelectric focusing was carried out using a LKB multiphor model 2117 with pre-cast LKB Ampholine Pagplates, pH. 3.5 to 9.5. The standards were bovine carbonic anhydrase (pI 6.57), myoglobin (pI 6.67 and 7.16), and lactate dehydrogenase (pI 8.55).

The molecular weight of the recombinant catalytic subunit was determined by gel filtration using a LKB Ultrogel AcA 44 column (1×116 cm). The running buffer was 25 mM potassium phosphate (pH 6.8), 200 mM KCl, and 0.2% sodium azide. The standards and their respective M values were ribonuclease A (13,700), chymotrypsinogen A (25,000), porcine catalytic subunit (38,000), ovalbumin (43,000), and bovine serum albumin (67,000).

The recombinant catalytic subunit was sequenced on a Applied Biosystems gas-phase sequencer as described in Example I.

EXAMPLE III

Purification of Mammalian Catalytic Subunit

Porcine hearts (40 hearts) were homogenized and then centrifuged. The supernatant (conductivity 3 mmho) was passed directly through a DE-23 column (4 L resin) equilibrated in 15 mM potassium phosphate, pH 6.5, 2 mM EDTA, 5 mM β-mercaptoethanol. The protein was eluted from the resin with buffer E (40 mM potassium phosphate, pH 6.5, 2 mM EDTA, 5 mM β-mercaptoethanol). The pooled kinase peak was immediately adjusted to a conductivity of 4 mmho at which point 1.5 L of DE-52 resin was added and the whole was mechanically stirred for 2 hours. The supernatant was poured off and the resin was poured into a column and washed extensively with buffer E, followed by extensive washing with buffer F (17 mM potassium phosphate, pH 6.1, 2 mM EDTA, 5 mM β-mercaptoethanol). The C-subunit was then eluted with 3 L of 220 μM cAMP followed by 8 L of buffer F and the eluent was passed through a CM-Sepharose column (50 mL volume) and then eluted with a linear gradient of buffer F containing 10% glycerol (250 mL) to 200 mM potassium phosphate, pH 6.1, 10% glycerol, 2 mM EDTA, 5 mM β-mercaptoethanol (250 mL).

EXAMPLE IV

Preparation of Labeled cAMP-Dependent Protein Kinase (a) Labeling subunits

Recombinant catalytic and regulatory subunits (approximately 0.5-2.0 mg/ml) of mammalian cAMP-dependent protein kinase were purified as described in Examples I and II and were dialyzed separately against 25 mM bicine pH 8.0, 0.1 mM EDTA for 4 to 5 hours at 0° C. The catalytic subunit was labeled with 0.3 mM fluorescein 5'-isothiocyanate (FITC; Molecular Probes, Eugene, Oreg.) in the presence of 8 mM $MgCl_2$ and 5 mM ATP to prevent inactivation of kinase activity. The regulatory subunit was labeled with 0.5 mM tetramethylrhodamine isothiocyanate (TRITC, isomer G; Molecular Probes, Eugene, Oreg.). Both labelings were allowed to proceed from 30 minutes at room temperature, then quenched by addition of 5 mM glycine for 10 to 15 minutes. The excess dye was removed by passing each protein solution through a Sephadex G-25 column (3 ml), eluted with 25 mM potassium phosphate pH 6.8, 2 mM EDTA, 5 mM 2-mercaptoethanol, 10% glycerol. The first colored or fluorescent band was collected.

The FITC-labeled catalytic and TRITC-labeled regulatory subunits (equal amounts by weight) were then mixed and dialyzed against 25 mM potassium phosphate pH 6.8, 0.5 mM $MgCl_2$, 0.1 mM ATP, 5 mM 2-mercaptoethanol, 5% glycerol for 3 to 5 days at 4° C. The formation of holoenzyme could be demonstrated by kinase assay measured using Kemptide as substrate (Slice & Taylor, ibid.).

(b) Labeling holoenzyme cAMP-dependent protein kinase holoenzyme (0.5-1.0 mg/ml) prepared from mammalian catalytic and recombinant regulatory subunits was dialyzed against 25 mM bicine pH 8.0, 0.1 mM EDTA at 4° C. $MgCl_2$ and ATP were added to give final concentrations of 8 mM and 5 mM respectively. The proteins were labeled with either fluorescein 5'-isothiocyanate or tetramethylrhodamine isothiocyanate (Isomer G) at final concentrations of 0.1–0.5 mM at room temperature for 20 to 30 minutes, followed by quenching with 5 mM glycine pH 8.0 for 10 minutes. Excess free dye was (partially) removed by passing the protein solutions through a column of Sephadex G-25 (3 ml), eluting with 10 mM potassium phosphate pH 6.7, 150 mM KCl, 5 mM 2-mercaptoethanol, 0.1 mM EDTA (Buffer I) and collecting the first colored fluorescent band.

The labeled holoenzymes were then passed through a cAMP affinity column (0.25 ml) (Wolfgang, W. et al., FEBS Lett. 99, 62 (1979)) at a rate of approximately 0.1 ml/minute and then eluted with 2 column volumes of the Buffer I at 4° C. The collected fractions contained labeled catalytic subunit. The column was eluted with Buffer I containing 1M KCl (2 column volumes) and the Buffer I (2 column volumes) again. These washes may contain some additional labeled catalytic subunit. To recover the labeled regulatory subunit, the column was eluted slowly with 30 mM cAMP in Buffer I (4 column volumes) at room temperature over a 2 hour period.

The differently labeled subunits were recombined in appropriate donor-acceptor pairs and dialyzed against several changes of 25 mM potassium phosphate pH 6.8, 0.5 mM $MgCl_2$, 0.1 mM ATP, 5 mM 2-mercaptoethanol, 5% glycerol for 3 to 5 days at 4° C. The formation of cAMPdPK holoenzyme could be monitored by loss of kinase activity, which can be recovered on addition of cyclic AMP.

EXAMPLE V

Titration of cAMP With Labeled Holoenzyme In Vitro

Figure 2:
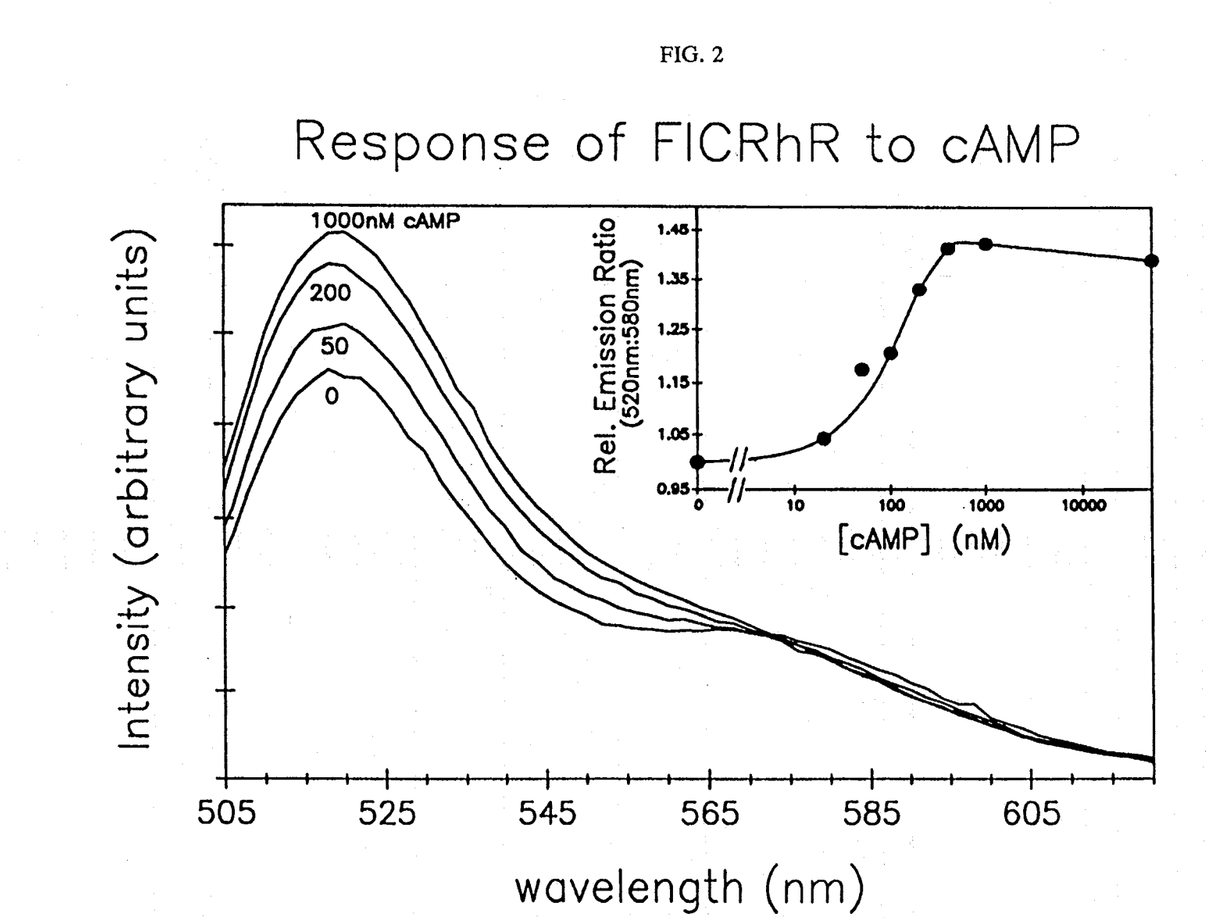
FIG. 2 shows the emission spectrum of labeled cAMPdPK at various concentrations of cAMP and the inset plots the ratio of emission at 520 nm to 580 nm at the various cAMP concentrations.

Holoenzyme (20 nM) labeled with 5'-fluorescein isothiocyanate (5'-FITC) on the catalytic subunit and tetramethylrhodamine isothiocyanate (isomer G) on the regulatory subunit, was dissolved in 135 mM KCl, 10 mM K.MOPS pH 7.2, 2 mM $MgCl_2$, 1 mM ATP at room temperature. The fluorescence emission was measured following excitation at 495 nm before and after addition of 20, 50, 100, 200, 400 nM, 1 and 51 μM cAMP (FIG. 2). Only the 0, 50, 200, 1000 nM cAMP spectra are shown in FIG. 1 for clarity. The calculated ratio of emission at 520 nm to 580 nm, normalized to the ratio at 0 cAMP is plotted with cAMP concentration in FIG. 2 (inset), indicated a half-maximal change in ratio as about 100 nM cAMP.

EXAMPLE VI

In Vivo Measurement of cAMP in Single Smooth Muscle Cells

Figure 3:
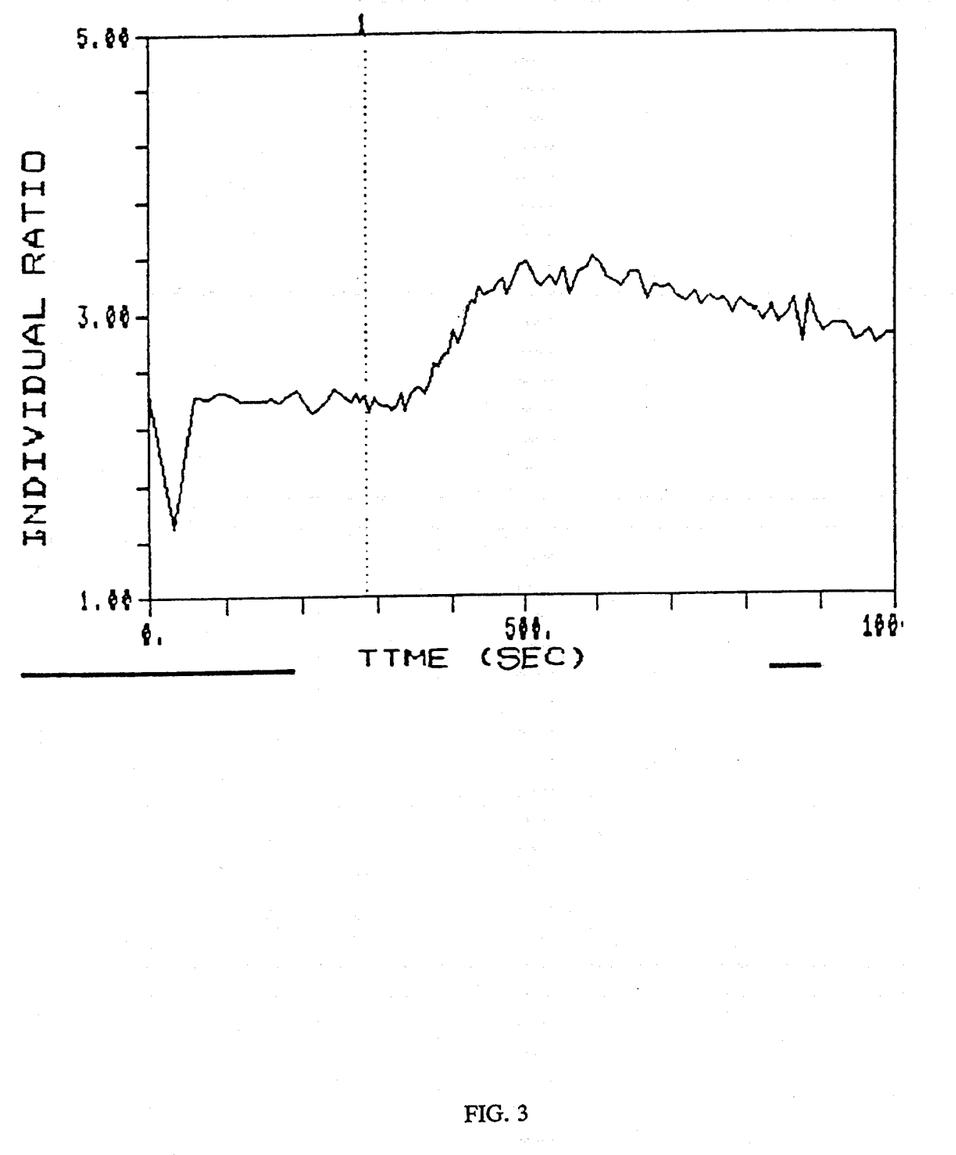
FIG. 3 shows the increase in cAMP concentration when a smooth muscle cell is treated with a membrane permeable cAMP analog.

Smooth muscle cells ($BC_3H_1$ cell line) were microinjected as described by Riabowol, Gilman & Feramisco, Cold Spring Harbor Symposia on Quantitative Biology, 53:85–90(1988), which is incorporated herein by reference, with 60 μM holoenzyme that was labeled with 5'FITC on the C subunit and TRITC on the $R^I$ subunit (FIG. 3). After 15 to 20 minutes, the cells were illuminated on a fluorescence microscope stage with 490 nm light at room temperature. The emitted light was detected by a Silicone Intensified Target camera (Dage-MTI; Michigan City, Ind. after passing through either a 500–530 nm bandpass filter or a 580 nm longpass filter. The two pictures per time point were digitised by an image processor, the ratio of 500–530 nm to >580 nm calculated at each pixel and displayed in pseudocolors on a television monitor. The average ratio in a representative cell was determined at each time point to give FIG. 3. At time point 1, 250 μM dibutyryl cAMP, a membrane-permeable cAMP analog, was added resulting in a gradual increase in ratio indicating a rise in cAMP analog inside the cell.

Figure 4:
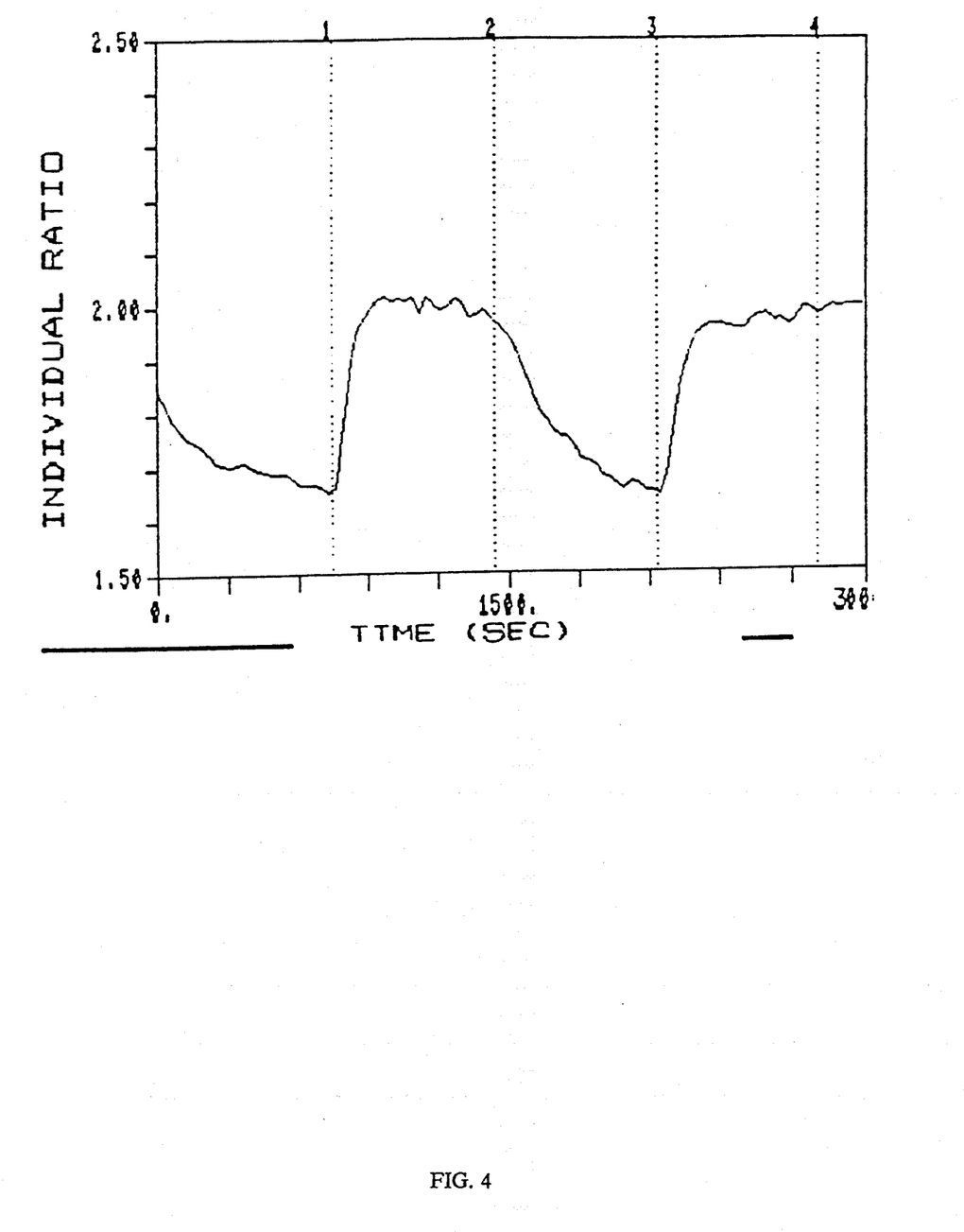
FIG. 4 shows the measurement of cAMP within a single cell when treated with various $\beta_2$-adrenergic agonists and antagonists.

In a separate experiment $BC_3H_1$ cells were microinjected and the emission ratio determined as described above. The following additions were made and are shown in FIG. 4 (1) 100 nM isoproterenol (2) 100 nM propranolol (3) 50 μM forskolin (4) 250 μM dibutyryl cAMP. Addition of isoproterenol, a $\beta_2$-adrenergic agonist elicited a rapid rise in emission ratio and therefore cAMP concentration within the cell, which was subsequently decreased by propranolol (a $\beta_2$-adrenergic antagonist). Direct activation of adenylate cyclase by forskolin caused a maximal emission ratio as no further effect was seen with dibutyryl cAMP, a membrane-permeable cAMP analog.

Although the invention has been described with reference to the presently-preferred embodiment, it should be understood that various modifications can be made without departing from the spirit of the invention. Accordingly, the invention is limited only by the following claims.

We claim:

1. A composition of matter, comprising $(S_1.A)_{n1}$ and $(S_2.D)_{n2}$, wherein $S_1$ is the regulatory subunit of adenosine 3', 5'-cyclic monophosphate dependent protein kinase and $S_2$ is the catalytic subunit of adenosine 3', 5'-cyclic monophosphate dependent protein kinase, and wherein D and A are different fluorochromes the emission wavelength of D overlapping the excitation wavelength of A, and D and A are in sufficiently close proximity to allow radiationless transfer of energy between the fluorochromes, and wherein n1 and n2 represent the stoichiometry of said subunits in said composition.

2. The composition of matter of claim 1, wherein D and A are selected from the group consisting of:
   fluorescein and tetramethylrhodamine,
   a 7-aminocoumarin and dipyrromethene-borate,
   an indocarbocyanine and rhodamine X, and
   a phycoerythrin and allophycocyanin,
   or derivatives thereof,
provided that the selected pair exhibit fluorescence energy transfer.

3. The composition of matter of claim 1, wherein the emission wavelength of D and the excitation wavelength of A are about 510 to 550 nm.

4. The composition of matter of claim 3, wherein the fluorochromes are fluorescein and tetramethylrhodamine or derivatives thereof.

5. The composition of matter of claim 1, wherein n1 is 2 and n2 is 2.

6. The composition of matter of claim 1, wherein $S_1$ and $S_2$ are recombinant proteins.

7. The composition of matter of claim 1, wherein one protein is a recombinant protein and one protein is derived from mammalian sources.

8. The composition of matter of claim 1, wherein $S_1$ and $S_2$ are derived from mammalian sources.

9. A composition of matter, comprising $(S_1.A)_{n1}$ and $(S_2.D)_{n2}$, wherein $S_1$ is the catalytic subunit of adenosine 3', 5'-cyclic monophosphate dependent protein kinase, and $S_2$ is the regulatory subunit of adenosine 3', 5'-cyclic monophosphate dependent protein kinase, and wherein D and A are different fluorochromes the emission wavelength of D overlapping the excitation wavelength of A and D and A are in sufficiently close proximity to allow radiationless transfer of energy between the fluorochromes, and wherein n1 and n2 represent the stoichiometry of said subunits in said composition.

10. The composition of claim 9, wherein D and A are selected from the group consisting of:
fluorescein and tetramethylrhodamine;
a 7-aminocoumarin and dipyrromethene-borate;
an indocarbocyanine and rhodamine X; and
a phycoerythrin and allophycocyanin, or derivatives thereof,
provided that the selected pair exhibit fluorescence energy transfer.

11. The composition of matter of claim 9, wherein the emission wavelength of D and the excitation wavelength of A are about 510 to 550 nm.

12. The composition of matter of claim 9, wherein $S_1$ and $S_2$ are recombinant proteins.

13. The composition of matter of claim 9, wherein one protein is a recombinant protein and one protein is derived from mammalian sources.

14. The composition of matter of claim 9, wherein $S_1$ and $S_2$ are derived from mammalian sources.

15. A method of determining the concentration of adenosine 3′, 5′-cyclic monophosphate in a sample comprising:
(a) forming the complex represented by the formula $(S_1 \cdot A)_{n1}$ and $(S_2 \cdot D)_{n2}$, wherein $S_1$ is the regulatory subunit of adenosine 3′, 5′-cyclic monophosphate dependent protein kinase and $S_2$ is the catalytic subunit of adenosine 3′, 5′-cyclic monophosphate dependent protein kinase, and wherein D and A are different fluorochromes the emission wavelength of D overlapping the excitation wavelength of A, and D and A in said complex are in sufficiently close proximity to allow radiationless transfer of energy between the fluorochromes, and wherein n1 and n2 represent the stoichiometry of said subunits in said complex;
(b) contacting the complex with the sample;
(c) exposing said sample to radiative energy near the excitation wavelength of D; and
(d) measuring the fluorescence emitted at the emission wavelength of at least one of D and A is.

16. The method of claim 15, wherein the measuring step comprises measuring the fluorescence emitted at the emission wavelength of both A and D, wherein the extent of energy transfer from D to A is determined by the ratio of the emission amplitude of A to the emission amplitude of D.

17. The method of claim 15, wherein the measuring step comprises measuring the fluorescence emitted at the emission wavelength of D and determining the extent of the energy transfer from D to A by the fluorescence lifetime of D or the rate of photobleaching of D.

18. The method of claim 15, wherein the sample comprises an intact cell and the contacting step comprises incorporating the complex into the cell.

19. The method of claim 18, wherein the contacting step is selected from the group consisting of microinjection, electroporation, lipofection, bead loading and scrape loading.

20. The method of claim 15, wherein D and A are selected from the group consisting of:
fluorescein and tetramethylrhodamine;
a 7-aminocoumarin and dipyrromethene-borate;
an indocarbocyanine and rhodamine X; and
a phycoerythrin and allophycocyanin,
or derivatives thereof,
provided that the selected pair exhibit fluorescence energy transfer.

21. The method of claim 15, wherein the emission wavelength of D and the excitation wavelength of A are about 510 to 550 nm.

22. The method of claim 20 or 21, wherein the fluorochromes are fluorescein and tetramethylrhodamine or derivatives thereof.

23. The method of claim 15, wherein n1 is 2 and n2 is 2.

24. The method of claim 15, wherein $S_1$ and $S_2$ are recombinant proteins.

25. The method of claim 15, wherein one protein is a recombinant protein and one protein is derived from mammalian sources.

26. The method of claim 15, wherein $S_1$ and $S_2$ are derived from mammalian sources.

27. A method according to claim 15, wherein the measuring step comprises measuring the fluorescence emitted at the emission wavelength of A, wherein the extent of energy transfer from D to A is determined by the amplitude of said emission.

28. A method of determining the concentration of adenosine 3′, 5′-cyclic monophosphate in a sample comprising:
(a) forming a complex represented by the formula $(S_1 \cdot A)_{n1}$ and $(S_2 \cdot D)_{n2}$, wherein $S_1$ is the catalytic subunit of adenosine 3′, 5′-cyclic monophosphate dependent protein kinase and $S_2$ is the regulatory subunit of adenosine 3′, 5′-cyclic monophosphate dependent protein kinase, and wherein D and A are different fluorochromes the emission wavelength of D overlapping the excitation wavelength of A, and D and A in said complex are in sufficiently close proximity to allow radiationless transfer of energy between the fluorochromes, and wherein n1 and n2 represent the stoichiometry of said subunits in said complex;
(b) contacting the complex with the sample;
(c) exposing said sample to radiative energy near the excitation wavelength of D and
(d) measuring the fluorescence emitted at the emission wavelength of at least one of D and A.

29. The method of claim 28, wherein the measuring step comprises measuring the fluorescence emitted at the emission wavelengths of both A and D, wherein the extent of energy transfer from D to A is determined by the ratio of the emission amplitude of A to the emission amplitude of D.

30. The method of claim 28, wherein the measuring step comprises measuring the fluorescence emitted at the emission wavelength of D and determining the extent of the energy transfer from D to A by the fluorescence lifetime of D or the rate of photobleaching of D.

31. The method of claim 28, wherein the sample comprises an intact cell and the contacting step comprises incorporating the complex into the cell.

32. The method of claim 31, wherein the contacting step is selected from the group consisting of microinjection, electroporation, lipofection, bead loading and scrape loading.

33. The method of claim 28, wherein D and A are selected from the group consisting of:
fluorescein and tetramethylrhodamine;
a 7-aminocoumarin and dipyrromethene-borate;
an indocarbocyanine and rhodamine X; and
a phycoerythrin and allophycocyanin,
or derivatives thereof, provided that the selected pair exhibit fluorescence energy transfer.

34. The method of claim 28, wherein the emission wavelength of D and the excitation wavelength of A are about 510 to 550 nm.

35. The method of claim 33 or 34, wherein the fluorochromes are fluorescein and tetramethylrhodamine or derivatives thereof.

36. The method of claim 28, wherein n1 is 2 and n2 is 2.

37. The method of claim 28, wherein $S_1$ and $S_2$ are recombinant proteins.

38. The method of claim 28, wherein one protein is a recombinant protein and one protein is derived from mammalian sources.

39. The method of claim 28, wherein $S_1$ and $S_2$ are derived from mammalian sources.

40. A method according to claim 28, wherein the measuring step comprises measuring the fluorescence emitted at the emission wavelength of A, wherein the extent of energy transfer from D to A is determined by the amplitude of said emission.

41. A method of preparing a labeled complex comprising ($S_1$.A) and ($S_2$.D), wherein $S_1$ is the regulatory subunit of adenosine 3', 5'-cyclic monophosphate dependent protein kinase and $S_2$ is the catalytic subunit of adenosine 3', 5'-cyclic monophosphate dependent protein kinase, and wherein D and A are different fluorochromes the emission wavelength of D overlapping the excitation wavelength of A, and D and A are in sufficiently close proximity to allow radiationless transfer of energy between the fluorochromes, said method comprising:

(a) mixing the labeled subunits $S_1$.A and $S_2$.D under conditions suitable for the formation of a complex comprising $\{(S_1.A)_{n1}.(S_2.D)_{n2}\}$, wherein n1 and n2 represent the stoichiometry of the labeled subunits in said complex; and wherein said fluorochromes are in sufficiently close proximity to allow radiationless transfer of energy between the fluorochromes; and (b) recovering the complex.

42. The method of claim 41, wherein the fluorochromes are fluorescein and tetramethylrhodamine, or derivatives thereof.

43. The method of claim 41, wherein $S_1$ and $S_2$ are recombinant proteins.

44. The method of claim 41, wherein one protein is a recombinant protein and one protein is derived from mammalian sources.

45. The method of claim 41, wherein $S_1$ and $S_2$ are derived from mammalian sources.

46. A method of preparing a labeled complex comprising ($S_1$.A) and ($S_2$.D), wherein $S_1$ is the regulatory subunit of adenosine 3', 5'-cyclic monophosphate dependent protein kinase and $S_2$ is the catalytic subunit of adenosine 3', 5'-cyclic monophosphate dependent protein kinase, and wherein D and A are different fluorochromes the emission wavelength of D overlapping the excitation wavelength of A, and D and A in said complex are in sufficiently close proximity to allow radiationless transfer of energy between the fluorochromes, wherein a first complex comprising $S_1$ and $S_2$ is attached to fluorochrome A, and a second complex comprising $S_1$ and $S_2$ is attached to fluorochrome D; wherein the subunits of said first and second complexes are separated to obtain labeled subunits $S_1$.D, $S_2$.D, $S_1$.A and $S_2$.A; said method comprising mixing said labeled subunits under conditions such that said fluorochromes come in sufficiently close proximity to allow radiationless transfer of energy between the fluorochromes to occur, resulting in the formation of labeled complexes $\{(S_1.D)_{n1}.(S_2.A)_{n2}\}$ or $\{(S_1.A)_{n1}.(S_2.D)_{n2}\}$, wherein n1 and n2 represent the stoichiometry of the labeled subunits.

47. The method of claim 46, wherein the fluorochromes are fluorescein and tetramethylrhodamine, or derivatives thereof.

48. The method of claim 46, wherein $S_1$ and $S_2$ are recombinant proteins.

49. The method of claim 46, wherein one protein is a recombinant protein and one protein is derived from mammalian sources.

50. The method of claim 46, wherein $S_1$ and $S_2$ are derived from mammalian sources.

51. A method of preparing a labeled complex comprising ($S_1$.A) and ($S_2$.D), wherein $S_1$ is the catalytic subunit of adenosine 3', 5'-cyclic monophosphate dependent protein kinase and $S_2$ is the regulatory subunit of adenosine 3', 5'-cyclic monophosphate dependent protein kinase, and wherein D and A are different fluorochromes the emission wavelength of D overlapping the excitation wavelength of A, and D and A in said complex are in sufficiently close proximity to allow radiationless transfer of energy between the fluorochromes, said method comprising:

(a) mixing the labeled subunits $S_1$.A and $S_2$.D under conditions suitable for the formation of a complex comprising $\{(S_1.A)_{n1}.(S_2.D)_{n2}\}$, wherein n1 and n2 represent the stoichiometry of the labeled subunits in said complex; and wherein said fluorochromes are in sufficiently close proximity to allow radiationless transfer of energy between the fluorochromes; and (b) recovering the complex.

52. The method of claim 51, wherein the fluorochromes are fluorescein and tetramethylrhodamine, or derivatives thereof.

53. The method of claim 51, wherein $S_1$ and $S_2$ are recombinant proteins.

54. The method of claim 51, wherein one protein is a recombinant protein and one protein is derived from mammalian sources.

55. The method of claim 51, wherein $S_1$ and $S_2$ are derived from mammalian sources.

56. A method of preparing a labeled complex comprising ($S_1$.A) and ($S_2$.D), wherein $S_1$ is the catalytic subunit of adenosine 3', 5'-cyclic monophosphate dependent protein kinase and $S_2$ is the regulatory subunit of adenosine 3', 5'-cyclic monophosphate dependent protein kinase, and wherein D and A are different fluorochromes the emission wavelength of D overlaps the excitation wavelength of the other A, and D and A in said complex are in sufficiently close proximity to allow radiationless transfer of energy between the fluorochromes, wherein a first complex comprising $S_1$ and $S_2$ is attached to fluorochrome A, and a second complex comprising $S_1$ and $S_2$ is attached to fluorochrome D; wherein the subunits of said first and second complexes are separated to obtain labeled subunits $S_1$.D, $S_2$.D, $S_1$.A and $S_2$.A; said method comprising mixing said labeled subunits under conditions such that said fluorochromes come in sufficiently close proximity to allow radiationless transfer of energy between the fluorochromes to occur, resulting in the formation of labeled complexes $\{(S_1.D)_{n1}.(S_2.A)_{n2}\}$ or $\{(S_1.A)_{n1}.(S_2.D)_{n2}\}$, wherein n1 and n2 represent the stoichiometry of the labeled subunits.

57. The method of claim 56, wherein the fluorochromes are fluorescein and tetramethylrhodamine, or derivatives thereof.

58. The method of claim 56, wherein $S_1$ and $S_2$ are recombinant proteins.

59. The method of claim 56, wherein one protein is a recombinant protein and one protein is derived from mammalian sources.

60. The method of claim 56, wherein $S_1$ and $S_2$ are derived from mammalian sources.

* * * * *

UNITED STATES PATENT AND TRADEMARK OFFICE
CERTIFICATE OF CORRECTION

PATENT NO. : 5,439,797
DATED : August 8, 1995
INVENTOR(S) : Roger Y. Tsien, et al.

It is certified that error appears in the above-indentified patent and that said Letters Patent is hereby corrected as shown below:

Column 13, line 61, replace "Silicone" with --Silicon--;

Column 13, line 62, replace "Ind." with --IN)--;

Column 15, line 26, replace "the" with --a--;

Column 15, line 43, omit "is";

Column 15, line 46, replace "wavelength" with --wavelengths--

Column 16, line 41, after "D" insert --;--;

Column 18, line 55, omit "the other".

Signed and Sealed this

Sixteenth Day of January, 1996

Attest:

BRUCE LEHMAN

*Attesting Officer*  *Commissioner of Patents and Trademarks*